Figure 1:
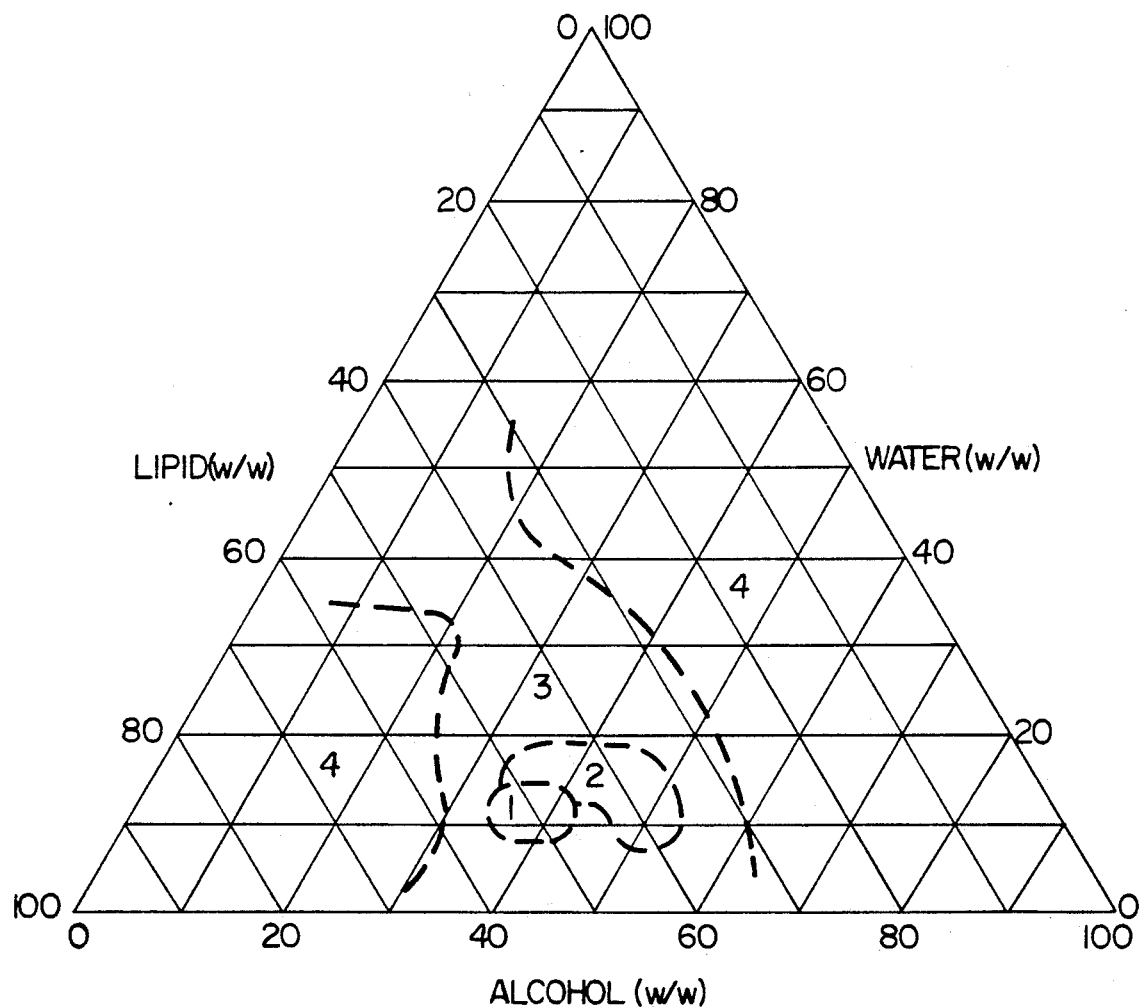

United States Patent [19]

Leigh

[11] Patent Number: 5,004,611

[45] Date of Patent: Apr. 2, 1991

[54] PRO-LIPOSOME COMPOSITIONS

[75] Inventor: Steven Leigh, Croydon, England

[73] Assignee: Phares Pharmaceutical Research NV, Curacao, Netherlands Antilles

[21] Appl. No.: 171,148

[22] Filed: Mar. 21, 1988

Related U.S. Application Data

[63] Continuation of Ser. No. 709,796, Mar. 8, 1985, abandoned.

[30] Foreign Application Priority Data

Mar. 8, 1984 [GB] United Kingdom ................ 8406038
Mar. 16, 1984 [GB] United Kingdom ................ 8406919

[51] Int. Cl.$^5$ ............................................. A61K 37/22
[52] U.S. Cl. .................................................... 424/450
[58] Field of Search ................ 424/417, 450; 264/4.1, 264/4.3, 4.6

[56] References Cited

U.S. PATENT DOCUMENTS 4,590,060  5/1986  Ehrenfeld ............................ 424/9

FOREIGN PATENT DOCUMENTS 130577   1/1985   European Pat. Off. .
0002404  2/1965   Japan ................................. 264/4.1
6089834  7/1981   Japan ................................. 264/4.1
2145107  3/1985   United Kingdom .
83/03383 10/1983  World Int. Prop. O. ............ 424/38

OTHER PUBLICATIONS

Chemical Abstracts 105: 12154c (1986).
Chemical Abstracts 103: 27287f (1985).
Chemical Abstracts 103: 156792r (1985), Hauser et al.

Primary Examiner—Douglas W. Robinson
Assistant Examiner—Raymond J. Henley, III
Attorney, Agent, or Firm—Wenderoth, Lind & Ponack

[57] ABSTRACT

Pro-liposome compositions comprise membrane lipids such as lecithin or distearyl dimethylammonium chloride, water-miscible solvents such as ethanol, optionally a minor proportion of water, and optionally fatty acid esters and drugs. On addition to excess water they spontaneously form dispersions of liposomes having high void volumes and high drug entrapment ratios.

Aerosol compositions are presented in a volatile liquid propellant. On being sprayed they form an aerosol of droplets which, on contact with aqueous media, spontaneously form liposome dispersions.

25 Claims, 3 Drawing Sheets

PRO-LIPOSOME COMPOSITIONS

This application is a continuation of now abandoned application Ser. No. 06/709,796, filed Mar. 8, 1985.

This invention relates to compositions based on membrane lipids, to a method of making lipid vesicles by the addition of aqueous liquid to the compositions, and to aqueous dispersions of the vesicles. Membrane lipids are lipids which form bilayers with water; they are chiefly phospholipids such as lecithin and related materials such as glycolipids. Phospholipid vesicles are also known as liposomes. According to the general nomenclature, all types of lipid bilayers surrounding an aqueous space are generally known as liposomes. An article by R. Firfield in New Scientist, 16th October 1980, pages 150 to 153 describes the preparation of liposomes from membrane lipids and says:

". . . Liposomes are microscopic bags (vesicles) that function like a cell membrane. Although liposomes are artificial entities, they display some biological properties, and as such they seem to be accepted into the environment of living cells. Some may merge with the cells own membrane and even function as if they were themselves organelles. . . so we can use liposomes to incorporate a wide range of materials that we choose to introduce into the cell, including medicines that can be accurately targeted to the site where they will have the greatest and most useful effect. Moreover, the wrapping material is biodegradable."

The promise held out by liposomes as a means of delivering and targeting drugs has, not surprisingly, prompted intensive research into this subject. However, difficulties have arisen which have hindered the commercial utilization of the valuable properties of liposomes. These difficulties are in summary:

1. Liposomes made by conventional techniques tend to be large multi-lamellar vesicles which contain only a relatively small volume of entrapped aqueous liquid. The concentration of drug (or other material) that can be introduced into such vesicles is seldom high enough to be useful.

2. Techniques are known for making liposomes in the form of unilamellar vesicles with large void volumes. But such techniques generally require complex equipment and careful control of conditions, and are not well suited to commercial operation.

3. Existing liposome dispersions are often unstable on storage, due to leakage and mechanical breakdown of the vesicles in suspension.

Some methods have been described in the literature aimed at improving the formation and entrapment efficiency of liposomes. Reference is drawn to a review on this subject by Szoka and Papahadjopoulos in "Liposomes: From Physical structure to Therapeutic Applications", Knight (ed.) Elsevier/North - Holland Biomedical Press, 1981, chapter 3. Three categories of liposome may be distinguished:

(i) Multi-lamellar vesicles comprise a whole series of concentric bilayers of membrane lipid with aqueous medium between the bilayers. They may be formed by dissolving a membrane lipid in an organic solvent, removing the solvent by evaporation to leave the lipid as a thin film, e.g. on the wall of a round bottom flask. Addition of aqueous buffer with agitation results in eventual formation of liposomes of various sizes up to 30 microns diameter. Because of the large number of bilayers in each vesicle, the amount of aqueous fluid entrapped is relatively small, of the order of 1 to 4 liters per mole of lipid, and drug entrapment ratios arc rather low, less than 20%. Vesicle size can be reduced by sonication, but this does not increase the entrapment ratio.

(ii) More vigorous sonication of multi-lamellar vesicles (MLV) results in the formation of small unilamellar vesicles (SUV), typically having diameters of 20 to 50 nm. SUVs can also be formed by rapid injection of a dilute solution of lipid in ethanol (maximum 3% by weight lipid) into an aqueous phase. SUVs typically have an aqueous void volume of from 0.2 to 1.5 liters per mole of lipid, and a drug entrapment ratio below 1%, far too low to be commercially useful.

(iii) Large unilamellar vesicles (LUV) may be formed by injecting a dilute solution of lipid in ether into aqueous fluid. Unlike the ethanol injection technique, the lipid concentration in the organic solvent does not appear to affect the size of the resulting liposomes. Thus this technique can give rise to vesicles having diameters in the range 0.15 to 0.25 microns and having an aqueous void space of 8 to 17 liters per mole of lipid. However, the drug entrapment ratio, at less than 1%, is still far too low to be useful.

LUVs can also be formed from water-in-oil emulsions of phospholipid and buffer in an excess organic phase, followed by removal of the organic phase under reduced pressure. This technique is reported to result in LUVs having diameters in the range 0.17 to 0.8 microns, void volumes in the range 4 to 14 liters per mole of lipid and drug entrapment ratios of 20 to 60%. But the preparative technique is difficult, requires complex equipment, and is not well suited to large-scale commercial operation.

In EPA 69307 there is described a method of producing liposome solutions by subjecting an aqueous solution of phospholipid to ultra-sonic radiation in the presence of an inert volatile solvent or gas. In Example 1, a solution of phospholipid in ethanol is subjected to ultra-sonic radiation on the addition of a large excess of water, and the aqueous dispersion subjected to further prolonged (75 minutes) ultra-sonic radiation. The method involves very vigorous treatment such as would not be practicable in commercial operation, and gives rise in our hands to dispersions of liposomes having low drug entrapment values.

This invention seeks to avoid the, problems of the prior art. It provides a pro-liposome composition, and a method of converting this to an aqueous liposome dispersion by simple addition of aqueous fluid with agitation. In the resulting liposome dispersion, which forms another aspect of the invention, the liposomes are generally oligo- or multi-lamellar vesicles with a void volume of at least 2 ml per gram of lipid, and capable of achieving a drug entrapment ratio of more than 20%, under preferred conditions more than 40%. The composition may also be provided in sprayable form to form an aerosol of droplets which, on contact with aqueous media, spontaneously form liposome dispersions.

In one aspect the invention provides a composition which spontaneously forms vesicles or liposomes in the presence of excess water, comprising a uniform mixture of:

(a) at least one membrane lipid,
(b) at least one water-miscible organic liquid which is a solvent for the lipid, and up to 40% by weight of water, the proportion by weight of (a) to (b) being from 40:1 to 1:20.

These compositions are progenitors of liposomes, or pro-liposomes. In another aspect, the invention also includes a method of forming an aqueous dispersion of liposomes, which method comprises mixing the dilutable pro-liposome composition with excess water.

In a further aspect, the invention also provides an aqueous liposome dispersion comprising liposomes formed of membrane lipid which have diameters in the range of about 0.1 to 2.5 microns and contain at least 2 ml of entrapped aqueous fluid per gram of the lipid, characterized by the presence in the aqueous dispersion of detectable quantities of a water-miscible organic liquid which is a solvent for the lipid.

The compositions of this invention may be presented in sprayable form. As a particularly advantageous aspect of this, the invention further provides aerosol compositions comprising in a volatile liquid propellant:
(a) at least one membrane lipid,
(b) at least one water-miscible liquid which is a solvent for the lipid, and
water, with up to 20%, by weight of the combined weights of (a), (b) and water,
the proportion by weight of (a) to (b) being from 40:1 to 1:20. These will be referred to hereafter as aerosol compositions.

Suitable membrane lipids are phospholipids, for example natural lecithins such as soy lecithin and egg yolk lecithin and synthetic lecithins e.g. di-palmitoyl phosphatidyl choline. Other materials such as glycolipids may be used. When the liposome dispersion is destined for internal medical use, the lipid must naturally be of pharmaceutically acceptable quality. When this is not the case, it is possible to use phospholipids of analytical grade or lower. Indeed, cheaper grades of phospholipid are sometimes easier to disperse in water than the chromatographically purified materials, and may be preferred for this reason. This is in contrast to the prior art which has generally considered it necessary to use highly purified lipid materials.

Other membrane lipids that can be used include long-chain dialkyl dimethyl ammonium compounds for example di-stearyl dimethyl ammonium compounds such as di-stearyl dimethyl ammonium chloride, and di-tallow dimethyl ammonium compounds such as di-tallow dimethyl ammonium chloride. These are synthetic materials which have the advantage of constant quality over lecithins and other naturally occurring materials, and are also less prone to oxidation.

When the compositions of this invention are intended for pharmaceutical use, component (b) needs to be nontoxic. Component (b) is preferably an aliphatic alcohol such as glycerol, propylene glycol, or, particularly, ethanol. Isopropyl alcohol, methanol, butanol and ethylene glycol may also be used when appropriate.

In the dilutable pro-liposome compositions, the proportion of component (a) to component (b) is from 40:1 to 1:20, preferably from 10:1 to 1:5, particularly from 2:1 to 1:2, by weight. Component (b) assists in the rapid formation of the liposomes, perhaps by influencing the hydration of the polar head groups of the membrane lipids. It also improves the entrapment efficiency of the system. If too little of component (b) is present, the switch-over to form liposomes on addition of water may be slow and the entrapment efficiency may be low. If too much of component (b) is present, the composition becomes a dilute solution of membrane lipid in organic liquid, which merely wastes organic liquid and reduces entrapment efficiency. On addition of excess water to the composition, component (b) mainly becomes dissolved in the continuous phase and plays no further part in the system.

The pro-liposome compositions preferably contain from 5% to 40%, particularly from 5% to 20%, by weight of water. Water serves two useful functions. First, the right proportion of water can enhance the spontaneity of liposome formation, when excess water is added, and can influence the liposome size and the entrapment efficiency of the system. Second, water can act as a carrier or solvent for a drug intended to be trapped in the inner water phase of the liposomes.

Particularly preferred dilutable pro-liposome compositions comprise from 35 to 55% by weight of component (a), from 30–55% by weight of component (b), and from 5 to 20% by weight of water. The compositions are readily diluted with water to form liposome dispersions of high entrapment efficiency.

The aerosol compositions of this invention generally contain from 5% to 40%, preferably 10% to 20%, of membrane lipid component (a); up to 40%, preferably up to 10%, of water component; balance ethanol or other water-miscible solvent, all percentages being by weight on the combined weights of components (a), (b) and water. Water is not critical to promote liposome formation as the pro-liposome is discharged as fine droplets, but may be useful when a water-soluble biologically active material is to be included. When ethanol is used as component (b), a minor proportion of propylene glycol or glycerol may be included to reduce possible volatility problems which might arise on spraying. Indeed, propylene glycol or glycerol may be used in partial or complete replacement for ethanol. The proportion by weight of membrane lipid component (a) to water miscible solvent component (b) is preferably from 1:2 to 1:10.

The aerosol compositions include a volatile liquid propellant which is preferably a perhalocarbon such as Arcton 12 ($CCl_2F_2$) or Arcton 114 ($C_2Cl_2F_4$). Butane may be used in circumstances where its use is permitted. The propellant generally constitutes from 50% to 95%, usually 60% to 80%, by weight of the overall composition. When a precisely metered dose of biologically active material has to be delivered, the proportion of propellant will generally be towards the upper end of this range.

On being sprayed, e.g. from an aerosol container, the propellant rapidly volatilises, leaving an aerosol of the remaining components as a pro-liposome composition in the form of droplets of a size determined by the spray nozzle and preferably below 8 microns. On contacting water, these droplets spontaneously form a dispersion of liposomes which constitute very effective drug carriers. This aspect of the invention is thus particularly suitable for aerosols for treating asthma, bronchitis or other respiratory tract problems. Examples of drugs as component (c) which may be incorporated in the sprayable compositions of this invention are salbutamol, terbutaline, orciprenaline, isoprenaline, reproterol, pirbuterol, budesonide, beclomethasone, di-proprionate, sodium chromoglycate, fenoterol, ipratropium, beta-methasone valerate, rimiterol, theophylline and ketotifen.

The pro-liposome compositions and the sprayable compositions of this invention may contain other non-volatile components in addition to (a), (b) and water. In particular, it is preferred to include up to 25% by weight [on the combined weights of components (a), (b) and water] of a fatty acid ester such as glyceryl tripalmitate or a sorbitan fatty acid ester, for example one of the materials sold under the Trade Mark SPAN. There is evidence that from 5 to 15% by weight of SPAN tends to increase entrapment efficiency by increasing void volume, and this effect is particularly marked when the cheaper grades of membrane lipid are used. While the reason for this effect is not understood, the fact that SPAN is particularly effective in samples subjected to excessive agitation suggests that the SPAN may also strengthen the liposomes in some way.

Cholesterol and other natural and synthetic vegetable fats and oils are conventionally added to liposome preparations, and may be included if desired in compositions according to this invention as replacements for up to about half the membrane lipid. High HLB surfactants, such as the range of materials sold under the Trade Mark TWEEN are not necessary and are not preferred, but may be included in compositions of this invention to counteract aggregation of liposomes in aqueous dispersion in amounts up to 1 to 2% by weight of components (a), (b) and water. Small quantities of materials which alter the net balance of charges, e.g. stearylamine and di-cetyl phosphate may also be included for this purpose in amounts up to about 20% by weight of components (a), (b) and water. Additives such as cholesterol, stearylamine, and cetyl phosphate may also improve liposome stability.

The liposome dispersions of this invention have pharmaceutical uses, for both internal and external application. They also have potential value in other fields, such as diagnostics, insecticides and horticulture. In recent years there has been increasing interest in the use of liposomes as carriers of compounds which are of interest because of one or other biological property, for example medicaments, proteins, enzymes, hormones, vitamins and marker compounds. It is to be understood that this broad group of biologically interesting compounds, which includes medicaments (human and veterinary) but is not restricted thereto, will be referred to in this specification as "biologically active compounds". In most cases, a biologically active compound needs to be included in a dilutable or aerosol composition. How this is done, in order to achieve maximum entrapment efficiency in the resulting liposome dispersion, depends on the properties of the active ingredient. Ingredients which are oil-soluble are best dissolved in the mixture of components (a) and (b). Ingredients which are insoluble may be dispersed, in the form of particles of sub-micron size, in the mixture of components (a) and (b). Ingredients which are water-soluble may be added as a concentrated aqueous solution to the mixture of components (a) and (b). The compositions of this invention are preferably prepared by first dissolving the membrane lipid in the organic solvent. This may be done at ambient or elevated temperature, preferably under nitrogen. Any other lipophilic components, e.g. SPAN or lipophilic drugs, should be added at this stage, then the required amount of water is added, and the mixture equilibrated. The term water is used here to include aqueous fluids, such as buffered solutions and solutions of active ingredients. Where a hydrophilic drug is being added, this should preferably be done by adding a solution of the ingredient in the minimum amount of water. After equilibration of this mixture, additional water may be added to provide a pro-liposome composition.

The pro-liposome compositions are mostly clear liquids at elevated temperatures around 50° to 60° C. Depending on their water content, some compositions show phase separation when cooled to ambient temperature. This phase separation is not harmful, and may even ease dispersion to form liposomes on addition of excess water. On addition of excess water (which term is again used to cover aqueous fluids, such as buffer solution) phase rearrangement takes place and a liposome dispersion is formed. Little or no agitation is required, although some limited agitation may improve dispersion. Excessive agitation may break up liposomes and reduce entrapment efficiency. Addition of excess water may be made at ambient or elevated temperatures, although dispersion may be quicker and easier at ambient temperature. Alternatively a fluid pro-liposome composition of this kind can be converted into a liposome dispersion by being sprayed into aqueous environment.

In most cases, economic considerations require that the method be performed to prepare liposomes that provide the highest possible entrapment of a limited amount of active ingredient (e.g. drug). Various conditions have to be optimized in order to maximize drug entrapment; pro-liposome preparation; dilution regimen; control of osmotic balance inside and outside the liposome; choice of membrane lipid; use of surfactants/stabilizers; modification of surface charge balance, etc. Lipid-drug ratios of 5:1 or less should be achievable using such approaches without too much difficulty.

In other cases, e.g. when the drug is cheap or readily reclaimable, entrapment efficiency may not be critical. In such cases, much higher levels of drug may be used, or the drug may be incorporated with the buffer used to form the liposome dispersion from the pro-liposome composition. If required, excess drug can be removed or recovered by filtration, dialysis or centrifugation.

The great majority of the resulting vesicles in the liposome dispersion have diameters within the range of 0.1 to 2.5 microns. The mean particle size generally averages out at 0.2 to 0.7 microns, and if further size reduction is desirable, the dispersion may be extruded through a membrane filter. The vesicles are often found to form two populations; a population of large particles having a mean diameter of about 1.8 microns and containing about one third of the entrapped aqueous fluid although the number of such particles is only about 5% of the total number; and a population of small particles having a mean diameter of about 0.2 microns and containing about two thirds of the entrapped aqueous fluid. The vesicles generally contain a few lipid bilayers and entrap at least 2 ml, and often 4 ml to 8 ml, of aqueous fluid per gram of membrane lipid. Void volumes herein have been measured by a standard procedure involving the addition of radioactively labelled insulin to the aqueous liposome dispersion. These liposome dispersions are characterized by containing detectable quantities of a water-miscible organic liquid which is a solvent for the lipid, namely component (b) of the starting pro-liposome or sprayable composition. Most liposome dispersions of the prior art do not contain any water-miscible organic liquids. Those that do, (e.g. those formed by the ethanol injection technique and according to EPA 69307) comprise vesicles of small size and small void volume.

A particularly attractive feature of this invention is that it may be applied to preparations for oral administration. For example, a pro-liposome composition may be placed inside a capsule which is then swallowed whole. Depending on the design of the capsule, the contents will be released somewhere in the gastrointestinal tract to form vesicles in-vivo. The drug remains protected within the lipid bilayers of the vesicles. It has been suggested that protecting a poorly absorbed, labile drug (e.g. insulin) in this manner could help absorption. In this connection, it has been noted that vesicles can form, irrespective of the ionic strength of the aqueous environment, in the range pH 3.2 to 8.6. It is assumed that any "free" drug remaining in the aqueous environment after spontaneous vesicle formation is non-toxic and need not be removed. Alternatively, the liposome dispersion can be generated in-vitro. Because of the simple preparative method, the dispersions can often be prepared immediately prior to use. This avoids a problem inherent in prior art liposome dispersions, namely poor storage stability. However, liposome dispersions according to this invention have shown good storage stability.

Reference is directed to the accompanying drawings, in which: FIG. 1 is a three-phase diagram for lipid/alcohol/water (L:A:W) showing regions yielding liposome dispersions having high glucose entrapment efficiency. FIG. 2 Freeze-fracture electron micrographs of replicas of liposomes prepared from formulation (L:A:W/50:40:10). FIG. 3. Diagrammatic representation of the steps involved in the formation of liposomes from pro-liposome compositions.

The following Examples illustrate the invention.

EXAMPLE 1

1. General Methodology and Nomenclature

Liposomes were prepared using the pro-liposome technique. This technique involves the addition of water to pro-liposome compositions prepared by combining lipid (lecithin), ethyl alcohol and water in appropriate ratios. These mixtures contained 5% (w/w) of glucose to act as a model for a water-soluble drug. The different formulations tested are identified by their basic proportions by weight of lecithin (L), alcohol (A) and water (W) e.g. (L:A:W/50:40:10). In all cases 10% (w/w) SPAN was added, and this component is considered to be additional to the basic formulation and its presence indicated separately.

2. Preparation of Pro-Liposome Compositions

Pro-liposomes were made up in 1-5 g batches. The appropriate weight of lecithin required to yield the desired formulation was first dissolved in the corresponding amount of alcohol at about 50° to 60° C. under $N_2$. The water fraction was then added in two parts. The first part consisted of the appropriate amount of glucose solution (500 mg/ml) required to yield a 5% (w/w) concentration of glucose and the second part the amount of distilled water required to make up the final formulation. 100 mg of SPAN per gram of formulation was added together with the lecithin. A typical formulation for 1 g of (L:A:W/50:40:10) plus 10% SPAN, would thus contain
500 mg lecithin (BDH egg-yolk)
400 mg (500 µl) ethyl alcohol
100 mg (100 µl) glucose (500 mg/ml) aqueous solution
100 mg SPAN The pro-liposome compositions were equilibrated for a further 15 minutes under $N_2$ moving to the liposome formation stage.

3. Preparation of Liposomes

Following equilibration, the pro-liposome compositions were cooled to 25° C. The liposomes were then prepared by a two-stage addition of 50 mM phosphate buffer (pH 7.4). In the first stage, 4 ml of buffer was added (per 1.1 grams of pro-liposome composition containing 10% SPAN). This addition was made dropwise and the sample was vigorously hand-shaken both during the addition and for 1 minute following the addition. The sample was then allowed to equilibrate for 30 minutes at 25° C. with further 1 minute periods of shaking after 15 and 30 minutes. The second addition of buffer, consisting of 6 ml of buffer per gram proliposome composition, was made at this stage and the sample equilibrated at 25° C. for a further 30 minutes. Again it was hand-shaken for 1 minute every 15 minute.

4. Measurement of Entrapment Efficiency

The efficiency of entrapment, calculated as the percentage of glucose added to the formulation retained within the liposomes, was estimated by separating the liposomes from excess untrapped glucose using a gel-filtration column and measuring the proportions of free and trapped glucose enzymatically.

Aliquots of 0.5 ml of liposome dispersion were passed down a filtration column (20 cm long × 1.0 cm diameter) containing Sephadex G-50 (fine) equilibrated with 50 mM phosphate buffer (pH 7.4). The liposomes were eluted using the same buffer. The liposome fraction, which was easily identified by its opalescence, was collected first and usually consisted of some 5 ml. A series of 3 ml fractions were collected after elution of the liposomes for analysis for free glucose.

5. Entrapment Efficiencies

The results of a typical series of measurements carried out using a wide range of formulations are listed in Table 1.

These were performed using ethanol. But it can be predicted that similar patterns will be found with other water miscible liquids, albeit with somewhat higher entrapment ratios, as indicated in Examples 16 to 19. Mixtures of solvents can be used.

When using solvents of higher molecular weight than ethanol, it may be found that more solvent is required (than would be the case when using ethanol) to ensure spontaneous liposome formation.

TABLE 1

| Entrapment efficiencies of a series of different pro-liposome formulations | |
|---|---|
| Formulation* (L:A:W) | Entrapment Efficiency |
| 54:35:11 | 45% |
| 55:35:10 | 41% |
| 50:40:10 | 41% |
| 45:40:15 | 36% |
| 40:20:40 | 35% |
| 50:35:15 | 34% |
| 50:37.5:12.5 | 34% |
| 40:50:10 | 30% |
| 40:45:15 | 30% |
| 54.5:36.5:9 | 29% |
| 45:45:10 | 28% |
| 50:12.5:37.5 | 28% |
| 50:10:40 | 28% |
| 40:40:20 | 28% |
| 40:30:30 | 26% |
| 50:25:25 | 25% |
| 50:30:20 | 24% |

TABLE 1-continued

Entrapment efficiencies of a series of different pro-liposome formulations

| Formulation* (L:A:W) | Entrapment Efficiency |
| --- | --- |
| 40:10:50 | 22% |
| 60:30:10 | 22% |

*All samples contained 10% (w/w) SPAN

The collected results of a series of such experiments have been used to plot the three-phase diagram of entrapment efficiency shown in FIG. 1. In this figure, region 1 denotes compositions yielding liposomes characterized by 40–50% glucose entrapment. Regions 2, 3 and 4 denote compositions which achieve 30–40%, 20–30% and below 20% glucose entrapment respectively. The reproducibility of results was good (±5%) using a given batch of BDH egg-yolk lecithin but interbatch variations were encountered.

Figure 2A:
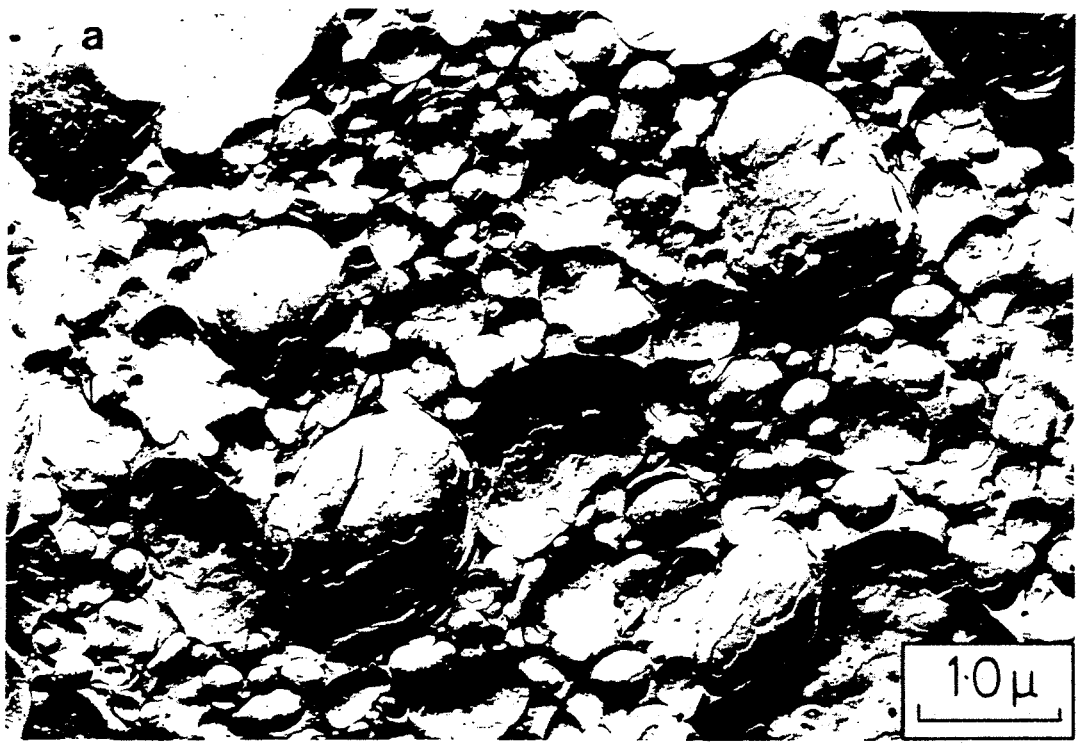
Figures 2B, 2C:
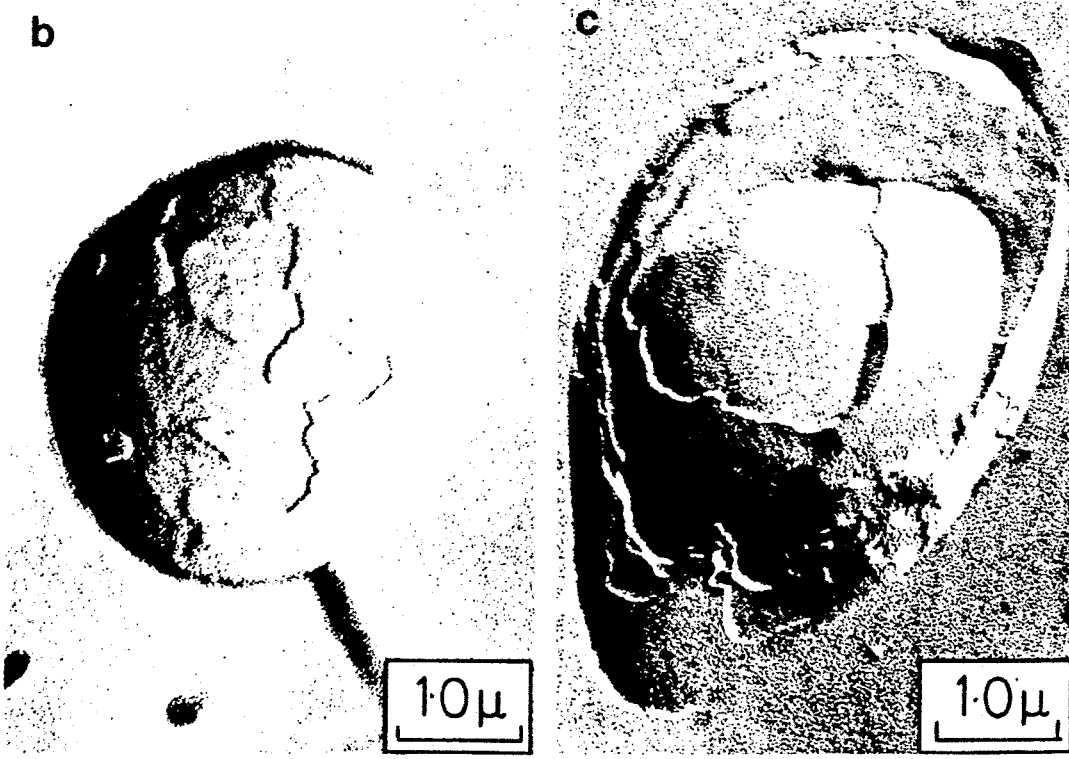
Figure 3A:
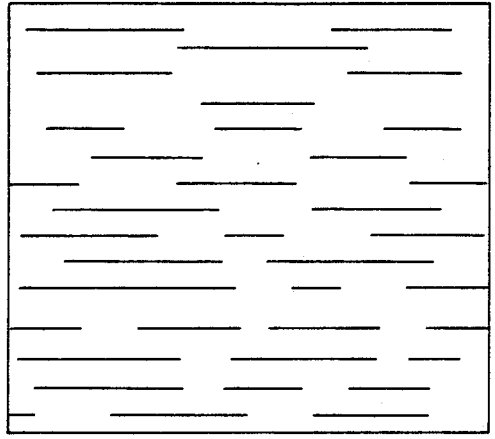
Figure 3B:
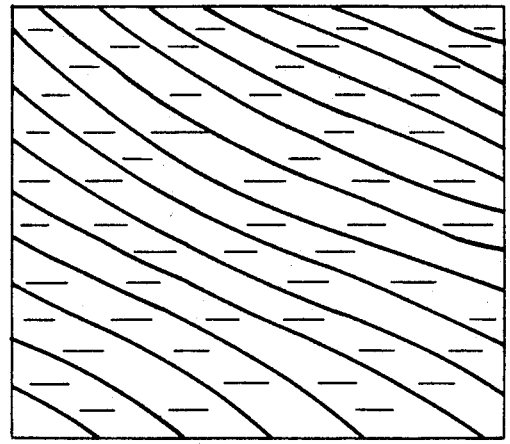
Figure 3C:
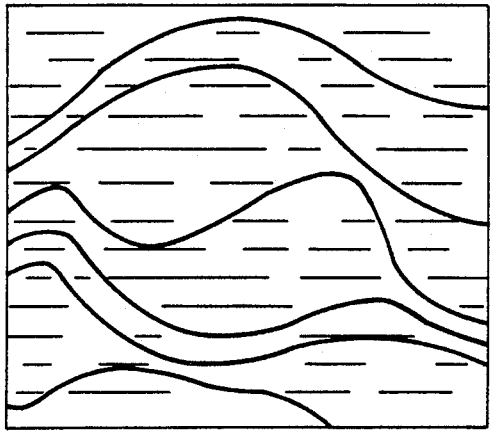
Figure 3D:
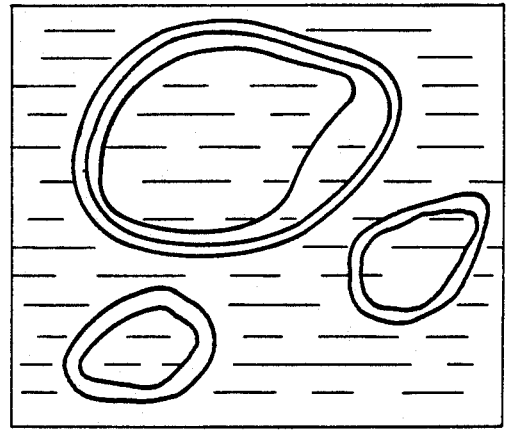

Interest has been concentrated on the liposomes formed from the (L:A:W/50:40:10) formulation. There is, however, no reason to suspect that liposomes formed from other formulations are different in structure. Typical electronmicrographs of freeze-fracture replicas of liposomes are shown in FIGS. 2a–c. The liposomes are normally 0.15–2.5μ in diameter and appear to consist of three or four bilayers around a central aqueous core. Cross-fracture views of liposomes indicate that they contain large enclosed aqueous volumes (FIG. 2c).

6. Sequence of Events Involved in Liposome Formation

The sequence of events following the addition of water (or buffer) to pro-liposome compositions has been examined using $^{31}P$ n.m.r. and electron microscopy. Most of the formulations used are clear liquids at elevated temperatures (50°–60° C.). Formulations containing little water remain clear when cooled to 25° C. but those with appreciable water (≧40%) tend to phase-separate. Depending on the rate of cooling this leads to the separation of a clear gel (slow cooling) or a fudge-like precipitate (rapid cooling). Mild agitation leads to a uniform consistency paste in both cases.

A similar phase-separation process occurs if excess water is added to the pro-liposome compositions at 25° C. $^{31}P$ n.m.r. measurements indicate that this separation corresponds to the formation of lipid bilayers. Precipitation of bilayer phase occurs following the addition of 30–40% (w/w) of water. Freeze-fracture electron microscopy indicates that the bilayers form as stacks and there is little indication of liposome formation. Pockets of liposomes are found in the freshly precipitated samples but they are comparatively rare. Addition of more water and agitation leads to formation of liposomes in the normal way. Few liposomes, however, are seen in samples containing less than 50–60% water.

A scheme illustrating the steps that appear to be occurring in liposome formation is presented in FIG. 3. The pro-liposome solution is normally a clear liquid (a), addition of small amounts of water leads to the formation of a network of expanded bilayers (b), further additions lead to the entrapment of water inclusions within the bilayers (c) and agitation leads to the breakdown of this structure to form liposomes (d). This scheme, which is consistent with the results of the n.m.r. and electron microscopy studies, accounts for the fact that the liposomes formed by the pro-liposome technique contain large aqueous spaces and tend to involve few thicknesses of bilayer. The role of the water-miscible organic liquid in this process is to ensure that the lipid initially precipitates as a loose network and to allow efficient penetration of excess water. The sequence of events will necessarily vary somewhat with different formulations of pro-liposomes. Samples with very high lipid concentrations will not go into solution easily and bilayer precipitation will lead to tightly packed bilayer stacks not easily penetrated by water. Samples containing high water contents will tend to be close to the final liposome stage whilst samples with very high alcohol content will be difficult to precipitate without using excessive quantities of water.

The pro-liposome method of the invention provides an exciting method of preparing large volumes of liposomes from cheap ingredients using simple technology. The liposomes formed by this method have large internal volumes and are ideal for the encapsulation of drugs. Incorporation of the drug in the pro-liposome composition allows high (30–40%) drug encapsulation with the minimum of wastage. Alternatively, if the drug is cheap and high entrapment efficiency is not required, the drug can be added together with the aqueous phase used in the formation of the liposome from the pro-liposome composition. Excess drug can then be removed, by filtration, dialysis or centrifugation leaving liposomes containing high concentrations of active ingredients.

EXAMPLES 2 TO 6

The following sprayable compositions were made up:

| Component | Concentration (wt %) | | | | |
| --- | --- | --- | --- | --- | --- |
| | Ex. 2. | Ex. 3. | Ex. 4. | Ex. 5 | Ex. 6 |
| Egg yolk lecithin | 20 | 15 | 20 | 15 | 15 |
| Span 40 | 5 | — | — | — | — |
| Water | 10 | 10 | 20 | — | 10 |
| Butylated hydroxytoluene | 0.1 | 0.1 | 0.1 | 0.1 | 0.1 |
| Theophylline | — | 1.0 | — | — | 1.0 |
| Salbutamol | — | — | 0.25 | — | — |
| Beclomethasone | 1.0 | — | — | 1.0 | — |
| Propylene glycol | — | 10 | — | 10 | 73.9 |
| Absolute alcohol | 63.9 | 63.9 | 59.65 | 73.9 | — |

One part by weight of the Example 2 or Example 5 formulation was mixed with 9 parts by weight of Arcton 12. An aerosol metering valve of 100 microlitre capacity delivered 100 micrograms of beclomethasone per dose.

Two parts by weight of the Example 3 or Example 6 formulation was mixed with 8 parts by weight of a mixture of Arcton 12 and Arcton 114. A 100 microlitre dose contains 200 micrograms of theophylline.

4 parts by weight of the Example 4 formulation was mixed with 6 parts by weight of Arcton 12. A 100 microlitre dose contains 100 micrograms of salbutamol.

EXAMPLES 7 TO 13

The procedure of Example 1, as described above in numbered paragraphs 1 to 4, was repeated using different drugs and different pro-liposome formulations. Except where stated below, the following standard pro-liposome formulation was used:

Egg yolk lecithin 500 mg
Span 40 100 mg
Ethyl alcohol 400 mg
Water containing drug 100 mg In all cases, centrifugation was used instead of gel-filtration to separate the two phases of the liposome suspension. The suspension was centrifuged at 100,000 G for 45 minutes. The supernatant liquid was assayed for drug content. The weights of the supernatant liquid and of the precipitate were recorded and the % of drug associated with the precipitate (% retention) calculated.

EXAMPLE 7

| | | |
|---|---|---|
| Drug | Glucose, at 25 and 250 mg/ml | |
| Retention | 18% | |

EXAMPLE 8

| | | |
|---|---|---|
| Drug | Tetracycline, at 6 and 60 mg/ml | |
| Retention | 43% | |

EXAMPLE 9

| | | |
|---|---|---|
| Drug | Carbocysteine, at 1 mg/ml | |
| Retention | 23% | |

EXAMPLE 10

| | | |
|---|---|---|
| Drug | p-Aminobenzoic acid, at 5 mg/ml | |
| Retention | 23% | |

EXAMPLE 11

| | | |
|---|---|---|
| Drug | Theophylline, at 5.9 mg/ml | |
| Retention | 24% | |

EXAMPLE 12

| | | |
|---|---|---|
| Drug | Theophylline, at 5.9 mg/ml | |
| Membrane lipid | Distearyl dimethylammonium chloride used in place of egg yolk lecithin | |
| Retention | 20% | |

EXAMPLE 13

| | | |
|---|---|---|
| Drug | Theophylline, at 5.9 mg/ml | |
| Pro-liposome formulation | Span 40 omitted | |
| Retention | 22% | |

EXAMPLE 14 TO 18

The procedure of Example 1, as described above in numbered paragraphs 1 to 4, was repeated using different pro-liposome formulations. Glucose was used to represent a drug. % retention of glucose was measured by dialysis.

EXAMPLE 14

| | | |
|---|---|---|
| Formulation | Egg yolk lecithin | 280 mg |
| | Cholesterol | 140 mg |
| | Dicetyl phosphate | 80 mg |
| | Ethyl alcohol | 400 mg |
| | Water containing drug | 100 mg |
| Drug Retention | Glucose, at 100 mg/ml 32% | |

EXAMPLE 15

| | | |
|---|---|---|
| Formulation | Egg yolk lecithin | 450 mg |
| | Glyceryl tripalmitate | 90 mg |
| | Ethyl alcohol | 370 mg |
| | Water containing drug | 90 |
| Drug Retention | Glucose, at 100 mg/ml 22% | |

EXAMPLE 16

| | | |
|---|---|---|
| Formulation | Egg yolk lecithin | 500 mg |
| | Ethylene glycol | 400 mg |
| | Water containing drug | 100 mg |
| Drug Retention | Glucose at 100 mg/ml 30% | |

EXAMPLE 17

| | | |
|---|---|---|
| Formulation | Phosphatidyl choline | 500 mg |
| | Ethyl alcohol | 400 mg |
| | Water containing drug | 100 mg |
| Drug Retention | Glucose at 500 mg/ml 40% | |

EXAMPLE 18

| | | |
|---|---|---|
| Formulation | Egg yolk lecithin | 500 mg |
| | Propylene glycol | 400 mg |
| | Water containing drug | 100 mg |
| Drug Retention | Glucose at 100 mg/ml 35% | |

EXAMPLE 19

| | | |
|---|---|---|
| Formulation | Egg yolk lecithin | 500 mg |
| | Isopropanol | 400 mg |
| | Water containing drug | 100 mg |
| Drug Retention | Glucose at 100 mg/ml 36% | |

I claim:

1. A pro-liposome composition comprising a uniform mixture of:
   (a) at least one membrane lipid and
   (b) at least one non-aqueous liquid consisting essentially of a water-miscible organic liquid which is a solvent for the lipid and
   (c) a biologically active compound and which, upon a step consisting essentially of the addition of a sufficient amount of water, spontaneously forms liposomes,
   the proportion by weight of (a) to (b) being from 40:1 to 1:20 and
   component (c) being present in an amount sufficient that a predetermined biologically effective dosage of the biologically active compound is associated with the liposomes.

2. The composition as claimed in claim 1, wherein there is also present a fatty acid ester in an amount of up to 25% by weight.

3. The composition as claimed in claim 1, wherein component (b) is ethanol or propylene glycol.

4. The composition as claimed in claim 1, wherein there is also present one or more of cholesterol, stearylamine and cetyl phosphate.

5. An aqueous liposome dispersion which is derived from a pro-liposome composition as claimed in claim 1, by the addition of water, and comprising liposomes formed of membrane lipid which have diameters within the range of about 0.1 to 2.5 microns and contain at least 2 ml of entrapped aqueous fluid per gram of the lipid, there being present in the aqueous dispersion detectable quantities of a water-miscible organic liquid which is a solvent for the lipid.

6. The pro-liposome composition according to claim 1 which additionally contains water, in an amount less than that which causes said composition to spontaneously form liposomes.

7. The pro-liposome composition as claimed in claim 6, wherein there is present from 5% to 40% by weight of water.

8. The pro-liposome composition as claimed in claim 6, wherein the proportion of component (a) is from 35% to 55% by weight, the proportion of component (b) is from 30% to 55% by weight and the proportion of water present is from 5% to 20% by weight.

9. An aerosol composition comprising in a volatile liquid propellant,
(a) at least one membrane lipid and
(b) at least one non-aqueous liquid consisting essentially of a water-miscible liquid which is a solvent for the lipid, and
(c) a biologically active compound, and which, upon a step consisting essentially of the addition of a sufficient amount of water spontaneously forms liposomes,
the proportion by weight of (a) and (b) being from 40:1 to 1:20 and
component (c) being present in an amount sufficient that a predetermined biologically effective dosage of the biologically active compound is associated with the liposomes.

10. The composition as claimed in claim 9, wherein there is also present a fatty acid ester in an amount of up to 25% by weight.

11. The composition as claimed in claim 9, wherein component (b) is ethanol or propylene glycol.

12. The composition as claimed in claim 9, wherein there is also present one or more of cholesterol, stearylamine and cetyl phosphate.

13. The composition as claimed in claim 9, wherein the proportion by weight of component (a) to component (b) is from 1:2 to 1:10.

14. The aerosol composition according to claim 9 wherein said composition additionally contains up to 40% by weight of water, based on the combined weights of (a), (b) and (c).

15. A method of making an aqueous dispersion of liposomes which consists essentially of mixing a pro-liposome composition comprising a uniform mixture of:
(a) at least one membrane lipid and
(b) at least one non-aqueous liquid consisting essentially of a water-miscible organic liquid which is a solvent for the lipid, and
(c) a biologically active compound,
the proportion by weight of (a) to (b) being from 40:1 to 1:20,
with sufficient water such that liposomes are spontaneously formed and
component (c) being present in an amount sufficient that a predetermined biologically effective dosage of the biologically active compound is associated with the liposomes.

16. A method as claimed in claim 15, wherein the resultant aqueous dispersion of liposomes is extruded through a membrane filter.

17. The method as claimed in claim 15, wherein the water is added at elevated temperature.

18. The method as claimed in claim 15, wherein the mixing step is performed in vitro.

19. The method as claimed in claim 15, wherein the mixing step is performed in vivo.

20. The method as claimed in claim 15, wherein the pro-liposome composition is contained inside a capsule which is swallowed whole such that the contents are released within the gastrointestinal tract and form liposomes in vivo.

21. The method according to claim 15 wherein there is additionally present water in an amount less than that which causes said composition to spontaneously form liposomes.

22. A method of making an aqueous dispersion of liposomes which consists essentially of spraying an aerosol composition comprising in a volatile liquid propellant:
(a) at least one membrane lipid and
(b) at least one non-aqueous liquid consisting essentially of a water-miscible liquid which is a solvent for the lipid, and
(c) a biologically active compound,
the proportion by weight of (a) to (b) being from 40:1 to 1:20, so that it comes into contact with sufficient water such that liposomes are spontaneously formed and
component (c) being present in an amount sufficient that a predetermined biologically effective dosage of the biologically active compound is associated with the liposomes.

23. The method according to claim 22 wherein there is present water in an amount of up to 40% by weight based on the combined weights of (a), (b) and (c).

24. A method of making an aqueous dispersion of liposomes from a pro-liposome composition as claimed in claim 1, which comprises the addition of water to form a network or stack of expanded bilayers, further additions of water leading to the entrapment of water inclusions within the said bilayers and agitation leading to the breakdown of this structure to form liposomes.

25. A composition as claimed in claim 1, in the form of an aerosol comprising droplets having an average diameter of below 8 microns.

* * * * *